United States Patent [19]

Rosini

[11] Patent Number: 4,578,376

[45] Date of Patent: Mar. 25, 1986

[54] PHARMACEUTICAL COMPOSITIONS FOR THE TREATMENT OF OSTEOPATHIAS

[75] Inventor: Sergio Rosini, Leghorn, Italy

[73] Assignee: Istituto Gentili S.p.A., Pisa, Italy

[21] Appl. No.: 677,177

[22] Filed: Dec. 3, 1984

Related U.S. Application Data

[63] Continuation of Ser. No. 527,373, Aug. 26, 1983, abandoned, which is a continuation of Ser. No. 342,780, Jan. 26, 1982, abandoned.

[30] Foreign Application Priority Data

Feb. 12, 1981 [IT] Italy ............................ 19673 A/81

[51] Int. Cl.$^4$ ............................................ A61K 31/66
[52] U.S. Cl. .................................................. 514/108
[58] Field of Search ................ 424/204; 514/102, 108

[56] References Cited

U.S. PATENT DOCUMENTS 4,134,969 6/1979 Schmidt-Dunker ............... 424/204
4,230,700 10/1980 Francis ............................ 424/222

OTHER PUBLICATIONS

Chem. Abstr. 97: 110192z, 1982.
Chem. Abstr. 98: 107557n, 1983.
Chem. Abstr. 97: 168913b, 1982.
Shinoda et al., Calcif. Tissue Int. 35: 87–99, 1983.

Primary Examiner—Albert T. Meyers
Assistant Examiner—John W. Rollins, Jr.
Attorney, Agent, or Firm—Bucknam and Archer

[57] ABSTRACT

A pharmaceutical composition for the treatment of osteopathias is described which contains an effective amount of the active ingredient 6-amino-1-hydroxyhexane-1,1-diphosphonic acid or a pharmaceutically acceptable salt, ester, or a chelation complex with copper and inert carriers. The compositions are suitable for oral or systemic administration or topical application.

8 Claims, No Drawings

PHARMACEUTICAL COMPOSITIONS FOR THE TREATMENT OF OSTEOPATHIAS

This is a continuation, of application No. 527,373, filed Aug. 26, 1983, now abandoned, which was a continuation of Ser. No. 342,780 filed Jan. 26, 1982, now abandoned.

The present invention relates to pharmaceutical compositions and more specifically to pharmaceutical compositions suitable for the treatment of osteopathia. The compositions of the present invention contains as the active agent, 6-amino-1-hydroxyhexane-1,1-diphosphonic acid and/or its salt, esters and chelation complexes with copper. Further, the invention relates to the use of the substance 6-amino-1-hydroxyhexane-1,1-diphosphonic cid and/or its salts, esters and chelation complexes with copper in the therapy of osteopathia. By the term "use", within the scope of the present invention, there is intended the use in all the operations connected with the preparation, the purification of the active agent, as well as its confection and/or its formulation in compositions and formulations suitable for the administration to patients affected by osteopathia.

It has been known for some time that low concentrations of condensed phosphates may prevent the deposition of calcium carbonate from solutions; in addition to this action, the condensed phosphates and among them the pyrophosphate are capable of inhibiting the precipitation of calcium phosphate when they are added even in very low concentrations to solutions of calcium phosphate.

This inhibitory action manifests itself both in solutions free of crystals of apatite, as well as in the presence of preformed crystals.

In addition, the condensed phosphates slow up the degree of transformation of calcium phosphate from the amorphous phase to the crystalline phase without influencing the formation of the amorphous phase. The significant effect of pyrophosphate (PP) on calcium phosphate in vitro in concentrations close to the concentration, which one finds in biological fluids, has suggested that the pyrophosphate may protect the soft tissue from mineralization. Further, in bones, PP could regulate the development of the same calcification so as to influence the transformation of calcium and phosphate. Another action of PP in bones already mineralized appears to be the influence of the degree of movement of calcium and phosphate towards the interior and exterior of the bones. In spite of all the knowledge which has been acquired with PP, its therapeutic use is prevented as a result of the rapid hydrolysis, which it undergoes when it is administered either by the oral route or by the systemic route. Due to this reason and the great interest in PP, many studies have been conducted at different times towards the preparation of substances with similar action, but resistant to hydrolysis. This object has now been at least partially achieved with the synthesis of diphosphonates, substances which contain a bond P-C-P instead of P-O-P. The effect of the diphosphonate on the calcium salts resemble closely the action induced by PP even in low concentrations; in fact:

they inhibit the precipitation of calcium phosphate from solutions;

they block the transformation of amorphous calcium phosphate into the crystalline phase, without, however, inhibiting the formation of the initial phase;

they block the aggregation of crystals of hydroxyapatite;

they slow up the degree of the dissolution of the crystals of hydroxy-apatite after the latter have absorbed the diphosphonate from the solutions.

Several pharmacological and clinical studies described in scientific literature show, however, that in spite of several similar features in activity, the various diphosphonates used up to the present time in the treatment of osteopathia exhibit some drawbacks, which are not negligible as far as the degree of toxicity in animals is concerned and the tolerability or the induction of side effects in humans.

It has now been surprisingly found that 6-amino-1-hydroxyhexane-1, 1-diphosphonic acid of formula I:

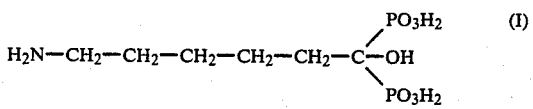

which will be referred to hereinbelow as AHEDP and its derivatives such as salts, esters and chelation complexes with copper are very suitable for the therapy of various forms of osteopathia, but is free of undesirable side effects, which occur in similar diphosphonates already known in the art. The compound (I) may be prepared by warming at a temperature between 80° C. and 90° C. for 3-4 hours, a mixture of 6-amino-hexanoic acid, orthophosphorous acid and phosphorous trichloride in the molar ratio of 1:1:2 in chlorobenzene. After cooling, the reaction mixture is poured into ice, chlorobenzene is eliminated with a current of gas, the product is cooled and filtered by suction. The solid so obtained is purified by dissolving in dilute NaOH, filtering and precipitating again with HCl at a pH of about 4.5.

The product of formula I is obtained as a white crystalline powder, contains one molecule of water of crystallization and melts at a temperature between 130° and about 230° C., depending upon the rate of heating. It is little soluble in water where it dissolves completely by addition of one equivalent of NaOH; it dissolves in HCl of average concentration. The elementary analysis data are in full agreement with the formula $C_6H_{17}NO_7P_2 \cdot H_2O$. The infrared spectrum in potassium bromide gives a complex band between 3700 and 2400 $cm^{-1}$, (a superimposition of stretching of the OH of the acid and alcohol and NH); 3000-2700 $cm^{-1}$ (stretching of $CH_2$ group); 1635 and 1520 $cm^{-1}$ (deformation of the amino group partially in the formation of salt due to the presence of the phosphonic groups; 1470 $cm^{-1}$ (deformation of $CH_2$); 1200 $cm^{-1}$ (stretching of associated P=O); 1150 $cm^{-1}$ (stretching of C-O of an alcoholic group); 1100 - 900 $cm^{-}$ (stretching of associated P-O); 85-700 (rocking of structurally differentiated $CH_2$); 600-400:(bands of the skeleton essentially due to that part of the chain which contains phosphorus atoms). NMR in $D_2O$ (neutralizing with NaOH): multiplet between 1.2 and 2.4 ppm, corresponding to $4CH_2$; idem at 2.8-3.1 ppm ($CH_2$ bound to $NH_2$); side bands due to water between 3.8 and 5.1 ppm.

The pharmaco-clinical and toxicological studies described hereinbelow show therapeutic properties of AHEDP.

Pharmacological and Toxicological Activity

The object of this study has been to investigate the effect of AHEDP on calvaria cells in culture, that is cells obtained from the skull cap of new born animals, the bone reabsorption and mineralization in vivo; the toxicity has also been estimated in mice.

1 - Experiments on "Calvaria" Cells

Cellular culture; the cells are first cultured in accordance with the method reported by Fast, et al., (Biochemical Journal, 172, 97–107 (1978). In short, calvaria removed from Wistar rats one day old has been digested with collagenase. The freed cells have been placed on plates in a concentration of 200.00 cells per ml of medium in Petri dishes of 3.5 cm diameter containing 1.5 ml of medium in dishes of 1.6 cm diameter containing 0.5 ml of medium. The cells have been cultivated in the essential minimum medium containing 10% of fetal calf serum in an atmosphere of 5% $CO_2$ at 37° C. up to the seventh or eighth day. The diphosphonates have been added on the first day up to the end of the experiment.

The cells have been counted with a Coulter counter after having been freed from the dishes by digestion with a mixture of collagenase and trypsin. On the seventh day, the mixture has been changed and the cells have been incubated for sixteen hours. The so obtained lactate during this period has been measured according to the method of Fast, et al.

2 - Experiments on the Bone Reabsorption and in Vivo Calcification

Groups of five Wistar rats of weight between 180 and 200 grams have been treated for seven days with 0.01, 0.1, 1.0 and 10 mg P/kg of AHEDP or with a physiological solution by the subcutaneous route. The animals have been fed with Altromine 1314 containing 1.1 gram per 100 grams of calcium, 1.2 grams per 100 grams P and 250 IU per 100 grams of Vitamin $D_3$. On the eighth day, the animals were killed and the tibia bones are removed and fixed in 50% ethanol. The tibia bones were then prepared for the histological examination and sections of 70-80$\mu$ thickness have been prepared for the microradiological study. This procedure has permitted an estimate of the mineral density in the metaphysis (Schenk, et al. Calc. Tiss. Res. 11, 196–214, 1973).

Results

On the basis of the concentrations used in the tests, in the first experiment only 250 $\mu$M of the composition have shown to have any effect because they cause some reductions, although slightly in the number of cells and increase in the production of the lactate. In stll lower concentrations, no negative effect is noted on the cellular behavior. On the basis of the experiments on the bone reabsorption and on the calcification, it has been possible to note that the dose of 0.01 mg of P/kg has no effect on the density of the bone while 0.1 mg and particularly 1 mg P/kg causes an increase in the density of the metaphyses, thus indicating a clear inhibition of the bone reabsorption. No treatment has shown any influence on the body weight, except in the dose of 10 mg P/kg, which obviously has no significant value.

The results so obtained show that the substance AHEDP is a powerful inhibitor of the bone reabsorption in a degree superior or similar to that of other well-known diphosphonates, in particular when one compares it with the analog, 3-amino-1-hydroxypropane-1,1-diphosphonate (APD), the substance exhibits a degree of cellular toxicity substantially inferior (about 100 times less), a fact which imparts to AHEDP a substantially superior margin of safety.

In vivo, the degree of toxicity of AHEDP has been determined in Swiss mice, both male and female by various routes of administration and by comparison with some of the best known and used diphosphonates.

On the basis of the tables below, it is clear that the substance AHEDP exhibits a low degree of toxicity in every route of administration. It is especially worth noting that particularly in comparison with the analog, the substance ADP, AHEDP exhibits superior tolerance. This report confirms what has already been reported in the in vitro experiments.

TABLE 1

Effect of AHEDP and the Analog, APD, on the Number of Cells in vitro and on the Production of the Lactate

| Compound | Concent. $\mu$M | No. of Cells % of control ± E.S. | Production of Lactate |
|---|---|---|---|
| AHEDP | 0.25 | 96.6 ± 1.7 | 99.4 ± 3.4 |
| " | 2.5 | 95.7 ± 7.8 | 90.7 ± 2.6 |
| " | 25 | 104.4 ± 2.1 | 95.7 ± 2.7 |
| " | 250 | 88.4 ± 1.5* | 139.0 ± 5.4* |
| APD | 2.5 | 90.8 ± 2.1* | 118.7 ± 3.1 |
| " | 25 | 64.9 ± 4.1* | 204.4 ± 10.8* |
| " | 250 | 0 | |

*Significance with respect to the control for PLO.001

TABLE 2

Values of $DL_{50}$ in Swiss mice both male and female of some diphosphonates. The values are expressed in mg/kg of body weight

| | OS (orally) | I.p. | I.v. |
|---|---|---|---|
| AHEDP | >2000 | 650 | 85 |
| APD | 625 | 190 | 45 |
| EHDP | 2000 | 250 | 35* |
| $Cl_2$MDP | >2000 | 780 | 75 |

*rats

EHDP = Ethane-1-hydroxy-1,1-diphosphonic acid disodium salt
APD = 3-Amino-1-hydroxypropane-1,1-diphosphonic acid disodium salt
$Cl_2$MPD = Dichloromethylenediphosphonic acid disodium salt.

Clinical Aspects

In view of the favorable pharmacological and toxicological results, the substance, AHEDP, has been tested clinically. The study deals with the effects on the metabolism of phosphorus and calcium of the new diphosphonate according to the present invention used in the treatment of demineralizing osteopathias, characterized by a high rate of bone reabsorption.

Number of Individuals Tested

Six individuals affected by the bone disease called Paget's condition, that is three men and three women of age between 52 and 68; three individuals affected by metastatic osteolysis, resulting from mammary carcinoma, that is three women between age 42 and 59 years old.

Dosage Administered and Period of Treatment

In eight cases, that is five individuals affected by Paget's disease and three individuals affected by osteolysis, the treatment has been carried out for fifteen days (in one of the cases of the individuals affected by Paget's disease, treatment continued for an additional fifteen days of therapy with a higher dosage); in the ninth case of the individual affected by Paget's disease, the treatment was continued for thirty days.

The first four cases, that is two individuals affected by Paget's disease and two individuals affected by osteolysis, have received dosage of AHEDP of 5 mg daily by the intravenous route (slow infusion); in the fifth case, the individual affected by Paget's disease, received a dose of 10 mg daily for fifteen days and then 20 mg daily for an additional period of fifteen days. Three other cases, that is two individuals affected by Paget's disease and one individual affected by osteolysis have been administered doses of 20 mg daily for fifteen days. The ninth individual affected by Paget's disease, has been treated with doses of 40 mg daily for 30 days.

Metabolic Parameters

Several parameters have been studied prior to the treatment, during the treatment and at the end of the treatment with respect to the metabolism of phosphorus and calcium and the tolerability of the substance.

(A) Metabolism of phosphorus and calcium:

calcemia, phosphatemia, alkaline phosphatasemia, plasmatic $PGE_2$, plasmatic iPTH, calciuria, phosphaturia, hydroxyprolinuria, cyclic nephrogenic AMP.

(B) Tolerability:

Hemochromocytometric examination, proteinemia, glycemia, azotemia, creatininemia, transaminasemia, immunoglobulin.

Results

In every case of individuals treated with the substance according to the present invention, it has been noted that the substance is well tolerated and has not caused significant variations in the parameters of tolerability, which have been studied: no side effects of any significance have been noted. As far as it concerns the parameters of the phosphorus and calcium metabolism, the substance has not caused variations worth mentioning with respect to the calcium and phosphate levels of the plasma at every dosage used; phases of hyperphosphatemia have not been observed and only in very short periods of some treatments, a low degree of calciemic contents have been noted; the treatments with 5-10-20-40 mg daily have not caused significant modification changes in the indexes of parathyroid activity (plasmatic immunoreactive PTH, cyclic nephrogenic AMP). Overall, a small increase of the se parameters has been noted, which has never reached significant levels. The treatment with 5-10 mg daily have not modified to a significant degree the urinary excretion of inorganic calcium and inorganic phosphates; significant increases of these two parameters have been observed with doses of 20-40 mg daily; this behavior has been obvious particularly in the case of phosphaturia; the high values of alkaline phosphatasemia present in all the individuals treated and the indexes of the increased osteoblastic activity have not been modified with dosages of 5-10-20 mg daily. A clear and rapid decrease of the alkaline phosphatasemia levels have been observed in the only case of an individual treated with 40 mg daily (Paget's disease in active phase).

Urinary Excretion of Hydroxyproline

It has been noted that the urinary excretion of hydroxyproline, which is an index of the catabolic processes of bone collagen and which is elevated in a substantial number of the individuals treated prior to the treatment, has been reduced to a significant extent in all the individuals treated: the decrease in hydroxyprolinuria is so much greater with respect to the values prior to treatment, the higher the dosage of the substance being administered. In three cases of the Paget's bone disease, there are present prior to treatment high plasmatic levels of $PGE_2$, which is the humoral factor of osteolysis. The treatment with 20–40 mg daily has caused a substantial and rapid decrease in the plasmatic $PGE_2$ in all three individuals. In one of these individuals, previous treatment with doses of 10 mg daily has not caused any change in this parameter.

Conclusions

Overall, the treatment with AHEDP has been tolerated in all cases and no undesirable side effects have been noted nor have substantial modifications of the hematic crasia and hepatic and renal functions been noted. The substance has shown to be effective in the prompt and progressive reduction of the urinary excretion of hydroxyproline, a fact which demonstrates the inhibitory effect of the processes of bone degeneration. Very interesting is the fact that doses of 5-10-20 mg daily, while blocking osteolysis, have not caused significant modifications in the plasmatic alkaline phosphatase and, therefore, in the osteoblastic activity of bone neodeposition; a reduction of both parameters has been noted only in the case of the individual treated with 40 mg daily of the substance.

A fact of particular importance and which confirms the high degree of tolerability and safety of the compositions of the present invention has been provided from the observation that in none of the individuals treated, there has been observed an increase of the body temperature or any variation in the hematic crasia.

Also, with respect to these parameters, the substance differs substantially from the analog, 3-amino-1-hydroxypropane-1,1-diphosphonate (APD), which on the other hand, causes substantial alterations in the parameters discussed hereinabove. These clinical results, which reaffirmed the pharmacological data, are of considerable value in a decision of using AHEDP therepeutically in osteopathias characterized by an increase in the processes of bone degeneration and in cases in which abnormal calcification or calcification on anomalous organs occur.

The substances of formula I, AHEDP, may be administered as such by the oral systemic and topical route. Pharmaceutical formulations suitable for administration may be the following:

Compresses, capsules, granulates, confections, by the oral route.

Drops by the oral route.

Solutions suitable for intramuscular, intravenous or intraarticular administration.

Creams for topical use.

The dosage with respect to the therapeutic use may be the following:

(a) 1-50 mg/kg of body weight by the oral route;
(b) 0.1-20 mg/kg of body weight in the systemic use;

(c) 1-10% by weight of active material with respect to the total weight of the formulations intended for topical use.

The excipients used for the solid formulations, that is granulates, operculated*capsules, compresses and confections, comprise the constituent substances, for instance in the case of operculated capsules, as well as additives commonly used pharmaceutically, such as diluents, powders, disassociating agents, lubricants, stabilizers and preservatives. By way of illustration, one can mention the following excipients: sugars, (such as saccharose, glucose, lactose, etc.); starches and derivatives, (such as maize starch, potato starch, etc.); cellulose and derivatives, (such as microgranular cellulose in powder, methylcellulose and ethylcellulose, carboxymethylcellulose); gums and gelatins, (such as arabic gum, gum tragacanth; fatty acids and derivatives, (such as stearic acid, magnesium stearate, calcium stearate or sodium stearate; polyhydroxy compounds (such as mannitol, sorbitol, polyethyleneglycol in the solid form); aromatic esters (such as methyl and propyl p-hydroxybenzoate, etc.); talcum, etc. *Operculated capsules are made by Parke-Davis. They are constituted by two small cylinders closed at one end, one small cylinder entering the other one, with the ends being spherical of the snap-fit type.

Among the excipients utilized for liquid formulations for instance, drops, one must mention liquid polyhydroxy compounds, such as a solution of sorbitol F.U., propyleneglycol, glycerin, etc. Naturally, purified water may also be used. In general, aqueous solutions of the active substance suitably neutralized, stabilized and deodorized may be used. Almost all the excipients necessary for the preparation of injectable solutions have already been mentioned among the excipients necessary for the preparation of liquid formulations by the oral route.

With respect to the formulations for topical use, that is suitable for direct application on the dermis or on the mucosae, the most suitable excipients comprise solvents such as sterile water and polyhydroxy compounds; fillers such as alcohols or fatty acids and their derivatives; emulsifiers such as polyethyleneglycol stearate, lecithin, Tweens and Spans; stabilizers such as phydroxybenzoate and propyl-gallate; and buffers. By way of examples, the following formulations may be mentioned:

| Operculated capsules - One capsule contains: | |
|---|---|
| AHEDP | 400 mg |
| Powdered Lactose | 45 mg |
| Talcum | 20 mg |
| Gelatin | 5 mg |
| Magnesium Stearate | 5 mg |
| Drops - 10 ml contains: | |
| AHEDP | 1 g |
| Neutralizing Agent | 1 ml |
| Stabilizing and Deodorizing Agent | Trace |
| Sterile Water g.b. | 10 ml |
| Injectable - 1 phthial contains: | |
| AHEDP | 20 mg |
| Sodium chloride | 40 mg |
| Sodium bicarbonate solution 0.1 N | 15 ml |
| Methyl parahydroxybenzoate | 5 mg |
| Sterile Water, g.b. | 5 ml |
| Granulate - one dose contains: | |
| AHEDP | 200 mg |
| Talcum | 10 mg |
| Magnesium Stearate | 2 mg |
| Silica gel | 4 mg |
| Maize starch | 9 mg |
| 3% Cream | |
| AHEDP | 3 g |
| Cetyl alcohol | 18 g |
| Propyleneglycol | 10 g |
| PEG monostearate | 4 g |
| Colesterin-stearate | 1 g |
| Linol-Linoleic acid | 1.5 g |
| Preservative and Stabilizers | 0.5 g |
| Distilled water g.b. | 100 g |

I claim:

1. The method of treatment of a patient affected by metastatic osteolysis or Paget's disease, which consists of administering to said patient a composition containing as the active ingredient 6-amino-1-hydroxyhexane-1,1-diphosphonic acid or a pharmaceutically acceptable salt thereof, in an amount between 10 mg and 40 mg daily.

2. The method according to claim 1 wherein the amount of said active ingredient in said composition is 1-50 mg/kg of body weight of said patient by the oral route.

3. The method according to claim 1 wherein the amount of said active ingredient in said composition is 0.1-20 mg/kg of body weight of said patient and the composition is administered by the systemic route.

4. The method according to claim 1 wherein the amount of said active ingredient per dose in said composition is 1-10% by weight of said active ingredient and the composition is administered by the topical route.

5. A pharmaceutical composition for the treatment of metastatic osteolysis or Paget's disease, which consists of an effective amount of the active ingredient 6-amino-1-hydroxyhexane-1,1-diphosphonic acid or a pharmaceutically acceptable salt thereof and at least one inert carrier.

6. A pharmaceutical composition according to claim 5 in the form of compresses, capsules, granulates or confections.

7. A pharmaceutical composition according to claim 5 in the form of a solution.

8. A pharmaceutical composition according to claim 5 in the form of a cream.

* * * * *